United States Patent [19]
Robinson et al.

[11] Patent Number: 5,996,426
[45] Date of Patent: Dec. 7, 1999

[54] END-SAMPLING THIEF PROBE

[75] Inventors: Priscilla A. Robinson, Dorado, Puerto Rico; Dean Brone, Green Brook, N.J.; Erinn K. Gleason, Fairfield, N.J.; Fernando J. Muzzio, Monroe, N.J.; Carolyn Wightman, Edison, N.J.

[73] Assignees: Merck & Co., Inc., Rahway; Rutgers, The State University of new Jersey, New Brunswick, both of N.J.

[21] Appl. No.: 08/944,289

[22] Filed: Oct. 6, 1997

Related U.S. Application Data

[60] Provisional application No. 60/029,631, Oct. 25, 1996.

[51] Int. Cl.$^6$ .............................. G01N 1/12; G01N 1/04
[52] U.S. Cl. .................................. 73/864.63; 73/864.45; 73/864.62; 73/864.64
[58] Field of Search ................................. 73/863, 863.31, 73/864.13, 864.14, 864.16, 864.18, 864.44, 864.45, 864.62, 864.63, 864.64; 405/241; 422/100; 175/20

[56] References Cited

U.S. PATENT DOCUMENTS

| | | | |
|---|---|---|---|
| 3,080,760 | 3/1963 | Piersma | 73/864.64 |
| 4,148,315 | 4/1979 | Berezkin et al. | 73/864.18 |
| 4,528,161 | 7/1985 | Eckert . | |
| 4,750,373 | 6/1988 | Shapiro . | |
| 4,989,678 | 2/1991 | Thompson | 175/20 |
| 5,045,286 | 9/1991 | Kitajima et al. . | |
| 5,063,025 | 11/1991 | Ito . | |
| 5,289,727 | 3/1994 | Earle et al. | 73/864.45 |
| 5,474,140 | 12/1995 | Stevens | 175/20 |
| 5,476,017 | 12/1995 | Pinto et al. | 73/864.62 |
| 5,478,526 | 12/1995 | Sakai et al. . | |
| 5,492,021 | 2/1996 | Bourgeois et al. | 73/864.45 |
| 5,512,248 | 4/1996 | Van . | |
| 5,703,301 | 12/1997 | Pinto et al. | 73/864.63 |

OTHER PUBLICATIONS

Ashton, M.D., et al., Trans. Instn. Chem. Engrs., vol. 44, pp. T166–188, 1966.
Lai, F., et al., Chemical Engineering Science, vol. 36, pp. 1133–1137, 1981.
Masiuk, S., Powder Technology, vol. 51, pp. 217–229, 1987.
Fan, L.T., et al., Powder Technology, vol. 61, pp. 255–287, 1990.
Schofield, C., Powder Technology, vol. 15, pp. 169–180, 1976.
Williams, J.C., et al., Chemical Engineer, vol. 269, pp. 19–25, 1973.
Orr, N.A., et al., Chemical Engineer, pp. 12–19, 1973.
Poole, K.R., et al., Trans. Instn. Chem. Engrs., vol. 42, pp. T305–T315, 1964.
Carley–Macauly, K.W., et al., Chemical Engineering Science, vol. 17, pp. 493–506, 1962.
Yip, C.W., et al., Powder Technology, vol. 16, pp. 189–192, 1977.
Poux, M., et al., Powder Technology, vol. 68, pp. 213–234, 1991.

*Primary Examiner*—Benjamin R. Fuller
*Assistant Examiner*—Robin Clark
*Attorney, Agent, or Firm*—Valerie J. Camara; Mark R. Daniel

[57] ABSTRACT

This invention relates to an end-sampling thief probe and a method of using this probe. The thief probe of the invention is useful in extracting a sample with minimal disturbance and provides an improved method for end-sampling.

6 Claims, 12 Drawing Sheets

(2 of 12 Drawing Sheet(s) Filed in Color)

END-SAMPLING THIEF PROBE

CROSS REFERENCE TO RELATED APPLICATIONS

This application is based upon U.S. Provisional Application No. 60/029,631 filed Oct. 25, 1996 (abandoned).

BACKGROUND OF THE INVENTION

Efficient blending and sampling of powders is of critical importance in the manufacture of a wide variety of pharmaceutical solid doses such as tablets and capsules. These products are manufactured from powder blends, granulated powders, and extruded pellets. In a typical process, powders, granules, and pellets are blended, discharged to a tote or drum, emptied into a hopper on a press or encapsulator, and divided into the final dosage form. Achieving and maintaining homogeneous and well characterized blends of powders and granules is of critical importance, especially in formulations involving small amounts of high potency components, which are a substantial fraction of all oral dosages. Inadequate mixing somewhere along the production sequence often results in rejection of finished product due to poor quality.

In many systems, the components requiring blending are usually powders of different size, density, shape, and cohesiveness. Since such materials often display a considerable tendency to segregate, ultimate mixture homogeneity cannot be taken for granted; quite the opposite, unless the blending process is properly designed and controlled, the result is often a mixture with significant composition fluctuations throughout the powder bed [See, L. T. Fan, Y.-M. Chen, and F. S. Lai, *Powder Technol.*, 61 (1990) 255. and M. Poux, P. Fayolle, J. Bertrand, D. Bridoux, and J. Bousquet, *Powder Technol.*, 68 (1991) 213.]. Inhomogeneities in the powder blend can result in increased variability in the contents of potent components in tablets, leading not only to decreased therapeutic value but also to direct health risks due to toxicity in super-potent tablets.

For the reasons mentioned above, a thorough understanding of blending processes is highly desirable. Unfortunately, blending of granular materials is largely an art rather than a science, and at the present time the ability to design and accurately evaluate the performance of a mixing process for a high potency drug is limited.

Characterization of mixtures in most industrial processes relies on taking and analyzing discrete samples. Parameters such as sample size (n), number of samples (N), and location of the sampling points can affect the measurement values. Guidelines for selecting the number of samples have been proposed based on theoretical random mixtures (i.e., >30) [Devore, J. L., *Probability and Statistics for Engineering and the Sciences*, Vol., Brooks/Cole Publishing Company, Monterey, 1982, p. 640] but optimal values of these parameters for real systems displaying incomplete mixing are often unknown.

In real mixtures, practical considerations and physical limitations of sampling mechanisms limit the number and size of the samples that can be obtained. Extensive sampling is often impractical; commonly, just a few samples (<30) are removed from a blender. The most common approach is to use a thief probe to withdraw samples from different locations in stationary powder mixtures.

Of signifcant interest are two essential sampling problems that cannot be easily solved using currently available commercial technology:

(i) Disturbances. The most common technique for obtaining samples is to use a thief probe. Available probes can introduce large errors in sample composition due to the massive disturbances that take place during insertion of the probe.

(ii) Segregation. It is well known among practitioners that powder mixtures can segregate (unmix) upon handling. Segregation can be a major sampling problem in any sampling process involving dry powders because such powders often segregate during insertion of the thief.

Thief samplers belong to two main classes: side sampling and end sampling. A typical side sampling probe has one or more cavities drilled or stamped in an inner cylinder enclosed by an outer rotating sleeve. The sleeve has holes that align with the cavities, allowing adjacent powder to flow into the cavities. Rotating the sleeve to its closed position traps the particles into the cavities. An end sampling thief has a single cavity at the end of the probe that can be remotely opened and closed. In both cases, the thief is introduced into the powder with its cavities closed. Once insertion is complete, the cavities are opened, allowing the powder to flow into them. The cavities are then closed, and thief is withdrawn, removing samples from the mixtures.

Thief sampling is a rather laborious and cumbersome technique and it is rarely practical to take more than 10 or 20 samples. In any sampling scheme, the experimentally measured variance, $\sigma_e^2$, is actually a combination of the true variance resulting from the mixing process, $\sigma_m^2$, the variance introduced by sampling error, $\sigma_s^2$ [Fan, L. T., et al., *Powder Technol.*, 61 (1990) 255], and the variance resulting from analytical analysis, $\sigma_a^2$, i.e., $$\sigma_e^2 = \sigma_m^2 + \sigma_s^2 + \sigma_a^2 \qquad (1)$$

In an ideal situation, $\sigma_s^2$ and $\sigma_a^2$ are negligible, and $\sigma_e^2$ (the variance subject to USP rules) is almost identical to $\sigma_m^2$ (the true variance). Unfortunately, thief probes bias measurements to the point that sampling uncertainty is expected to be a large fraction of the measurement [Ashton, M. D., et al., *Trans. Instn. Chem. Engrs.*, 44 (1966) T166; Schofield, C., *Powder Technol.*, 15 (1976) 169; Yip, C.W., et al., *Powder Technol.*, 16 (1977) 189; Lai, F., et al., *Chem. Eng. Sci.*, 36 (1981) 1133]. As mentioned earlier, two type of errors are often introduced by thief probes: (i) the mixture is extensively disturbed when the thief probe is inserted into the powder bed, and (ii) particles of different sizes often flow unevenly into the thief cavities. Side-sampling probes often have an additional problem: cohesive powders do not flow easily into thief cavities, sometimes resulting in samples that are smaller than desired.

Only a few studies have attempted to quantify the errors introduced by thief probes mainly focusing on side-sampling thief probes [Carley-Macauly, K. W., et al., *Chem. Eng. Sci.*, 17 (1962) 493; Schofield, C., *Powder Technol.*, 15 (1976) 169; Poole, K. R., et al., *Trans. Instn. Chem. Engrs.*, 42 (1964) T305; Masiuk, S., *Powder Technol.*, 51 (1987) 217; Gopinath, S., 27 (1982) 321; Gayle, J. B. et al., 50 (1958) 1279]. Carley-Macauley and Donald [Carley-Macauly, K. W., et al., *Chem. Eng. Sci.*, 17 (1961) 493] performed a comparison study between two types of side sampling probes. One was a conventional probe (as described above); the other probe had cavities that were closed using a longitudinal slit. They took samples from a system composed of sand of two colors arranged in a layered structure. The conventional probe gave samples of a mixed color within a region of two aperture diameters (0.13") from the layer boundary. In the longitudinal slit probe, sand particles tended to run down the slit, causing errors greater than the conventional side sampling probe. In both cases, errors occur because the probe is sampling locations that have already been disturbed by the insertion of the probe itself. Other studies have reached similar conclusions. For example, in a study conducted by Williams and Khan [Williams, J. C., et al., *Chem. Eng.*, (1973) 19], although no quantitative data was reported, the authors concluded that a side sampling thief gave totally misleading results in a segregating system. Instead, they used a sampler that removed a core of powder from the bed. The sampler was divided into sections in order to divide the core into samples. Orr and Shotton [Orr, N. A., et al., *Chem. Eng., London*, January (1973)12] determined that perturbations of the mixture structure are caused by friction along the length of the probe, and are independent of the profile of the tip. This result suggests that an end sampling probe will perform better than a side sampling probe because for an end-sampling probe the sample is taken from a relatively undisturbed region of powder beneath the tip of the probe. They developed such a probe for use with cohesive powders. Components sampled at depths of 1, 2, 4 and 6 cm through a 2 cm layer of charcoal powder qualitatively showed little contamination of the samples with charcoal powder. In a quantitative analysis, 20 samples of cohesive calcium carbonate were taken through a layer of cohesive lactose at a depth of 2 cm below an interface. The maximum amount of lactose found in the samples was 0.07% [Orr, N. A., et al., *Chem. Eng., London*, January (1973)12].

SUMMARY OF THE INVENTION

This invention relates to an end-sampling thief probe and the method of using this thief probe. This end-sampling thief is a useful tool for extracting samples with a minimal amount of disturbance to the powder bed allowing for a more accurate analysis of the mixing of powders. The design of the aperture for this end-sampling thief probe provides this probe with a mechanism for extracting a more accurate core sample.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
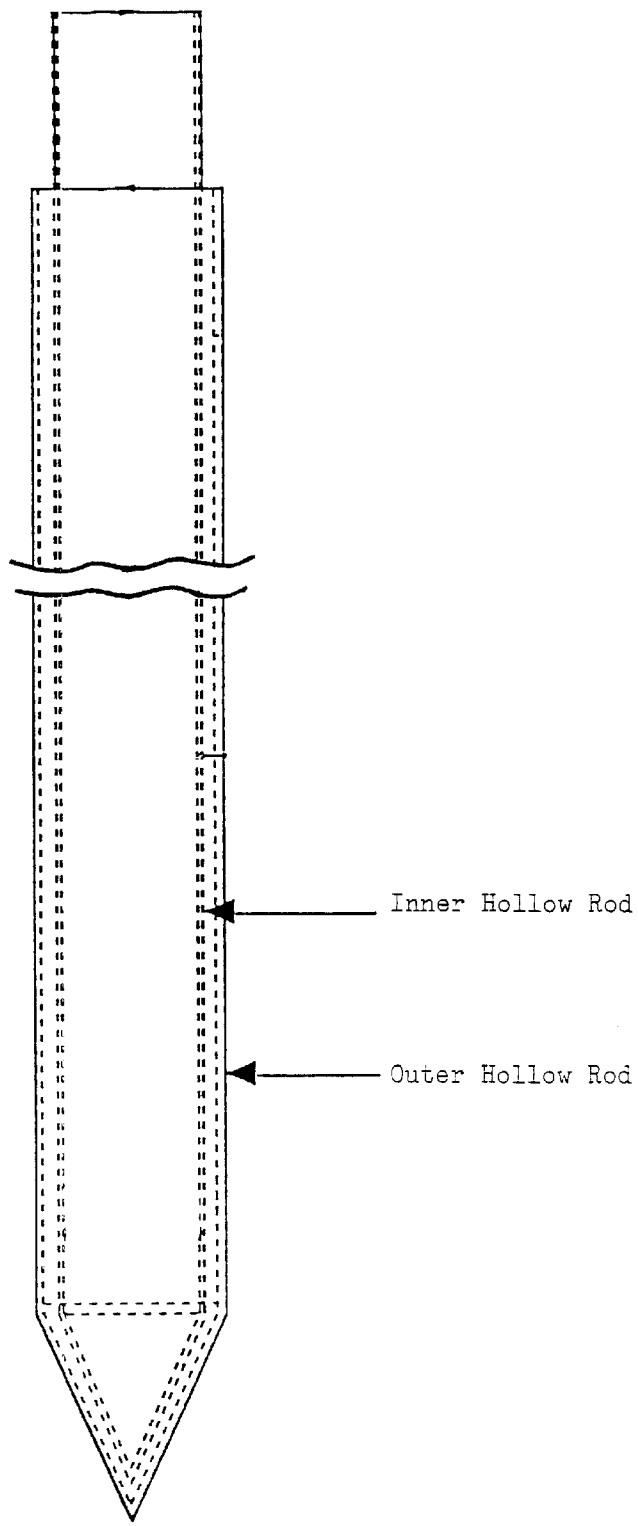
FIG. 1. Schematic of the inner hollow rod with a inner conical tip mounted in the outer hollow rod with a outer conical tip of the thief probe of the invention (front view).
Figure 2:
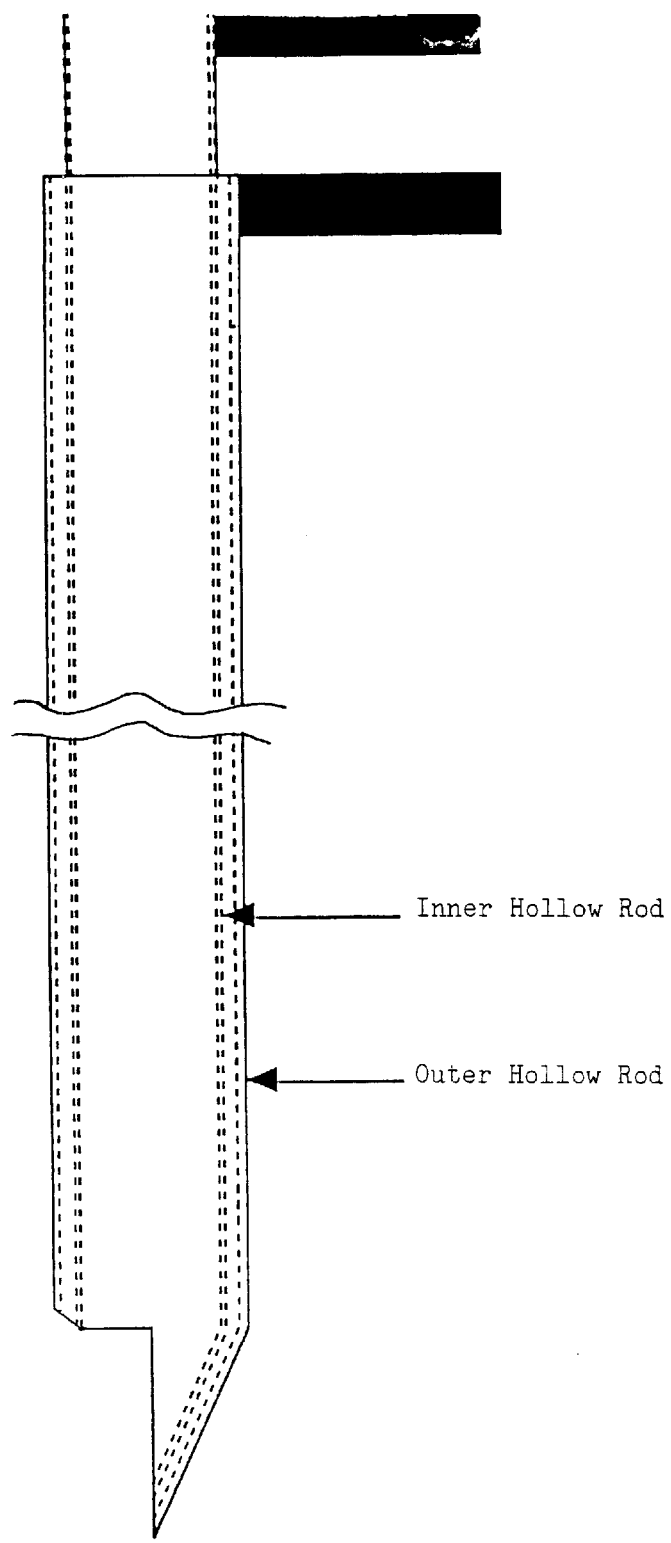
FIG. 2. Schematic of the inner hollow rod with a inner conical tip mounted in the outer hollow rod with a outer conical tip of the thief probe of the invention in the open position (side view).
Figure 3:
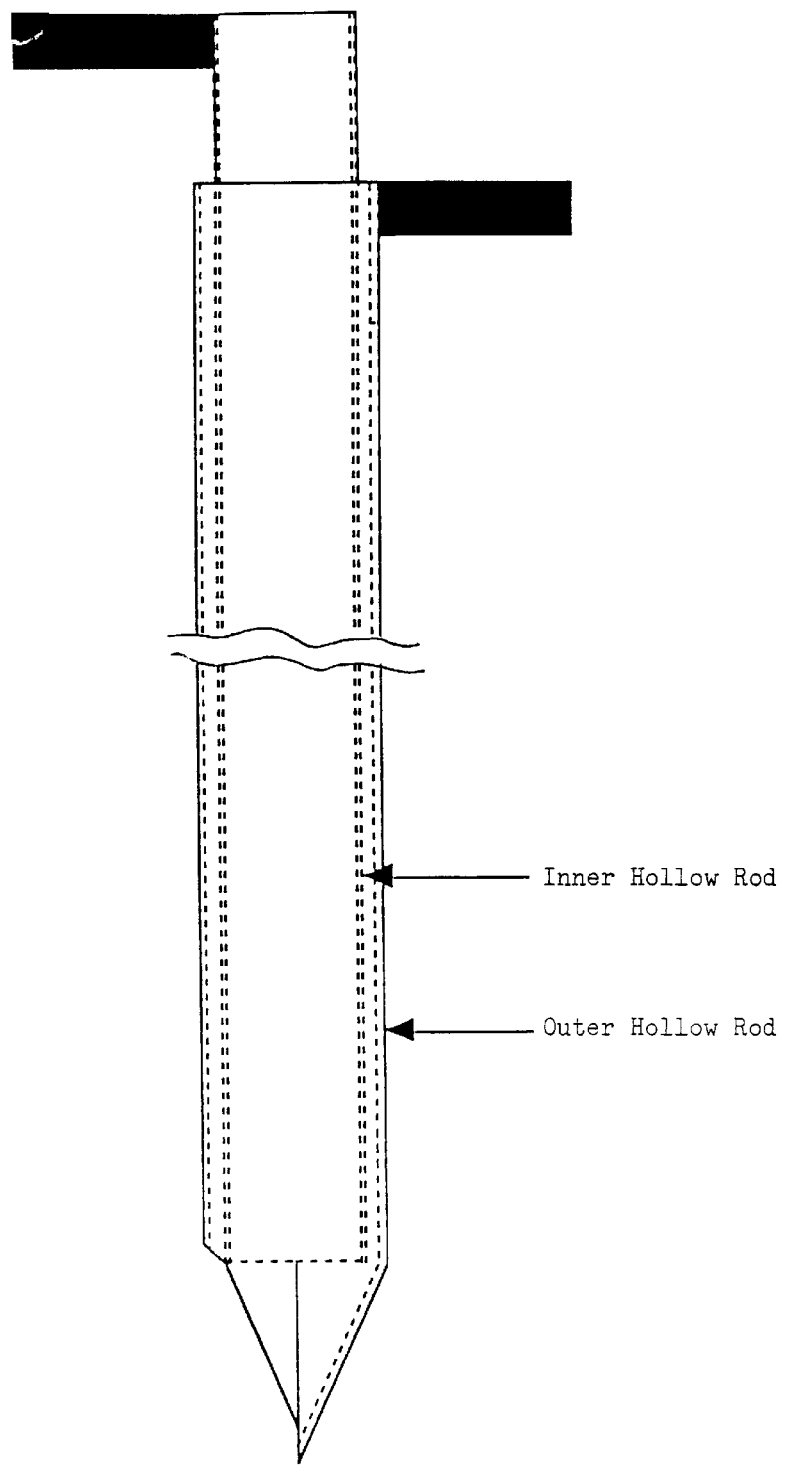
FIG. 3. Schematic of the inner hollow rod with a inner conical tip mounted in the outer hollow rod with a outer conical tip of the thief probe of the invention in the closed position (side view).

A thief probe comprising an outer hollow rod with a hollow conical tip attached at one end of the outer hollow rod and an inner hollow rod with a conical tip attached at one end of the inner hollow rod;

said outer hollow rod having an inner diameter of about ¼ in. to about $^{63}/_{32}$ in. and an outer diameter of about $^{9}/_{32}$ in. to about 2 in.;

the hollow conical tip of the outer hollow rod having an aperture;

the aperture of the hollow conical tip of the outer hollow rod being up to about ½ of the surface of the hollow conical tip; said inner hollow rod having an inner diameter of about $^{7}/_{32}$ in. and an outer diameter of about $^{62}/_{32}$ in.;

the hollow conical tip of the inner hollow rod having an aperture;

the aperture of the hollow conical tip of the inner hollow rod being up to about ½ of the surface of the hollow conical tip;

the outer hollow rod being shorter in length than the inner hollow rod by about 3 in.;

the inner hollow rod being mounted in the outer hollow rod and rotatable about the axis of the inner and outer hollow rods;

said inner and outer hollow rods being rotatable to an open position and a closed position;

the open position being defined as the point where the apertures of the hollow conical tips of the inner and outer hollow rods are aligned so as to expose the cavity in the hollow conical tip of the inner hollow rod; and the closed position is the point where the inner and outer apertures of the inner and outer hollow conical tips are aligned so as not to expose the cavity in the hollow conical tip of the inner hollow rod.

An embodiment of the invention is a thief probe comprising an outer hollow rod with a hollow conical tip attached at one end of the outer hollow rod and an inner hollow rod with a inner hollow conical tip attached at one end of the inner hollow rod;

said outer hollow rod having an inner diameter of about ¼ in. to about $^{63}/_{32}$ in. and an outer diameter of about $^{9}/_{32}$ in. to about 2 in.;

the hollow conical tip of the outer hollow rod having an aperture;

the aperture of the hollow conical tip of the outer hollow rod being up to about ½ of the surface of the hollow conical tip; said inner hollow rod having an inner diameter of about $^{7}/_{32}$ in. to about $^{61}/_{32}$ and an outer diameter of about $^{8}/_{32}$ in. to about $^{62}/_{32}$;

the hollow conical tip of the inner hollow rod having an aperture;

the aperture of the hollow conical tip of the inner hollow rod being up to about ½ of the surface of the hollow conical tip;

the outer hollow rod being shorter in length than the inner hollow rod by about 3 in.;

an inner solid rod having a diameter of 9/32 in. to about 60/32 in.;

said inner solid rod being mounted in the inner hollow rod and being adjustable in height, so as to define the size of the cavity of the inner hollow rod;

the inner hollow rod with the mounted inner solid hollow rod being mounted in the outer hollow rod and rotatable about the axis of the inner and outer hollow rods;

said inner and outer hollow rods being rotatable to an open position and a closed position;

the open position being defined as the point where the apertures of the hollow conical tips of the inner and outer hollow rods are aligned so as to expose the cavity in the hollow conical tip of the inner hollow rod; and the closed position is the point where the inner and outer apertures of the inner and outer hollow conical tips are aligned so as not to expose the cavity in the hollow conical tip of the inner hollow rod.

An embodiment of the invention is a thief probe comprising an outer hollow rod with a hollow conical tip attached at one end of the outer hollow rod and an inner hollow rod with a inner hollow conical tip attached at one end of the inner hollow rod;

said outer hollow rod having an inner diameter of about 7/16 in. and an outer diameter of about 8/16 in.;

the hollow conical tip of the outer hollow rod having an aperture;

the aperture of the hollow conical tip of the outer hollow rod being up to about ½ of the surface of the hollow conical tip;

said inner hollow rod having an inner diameter of about 11/32 in. and an outer diameter of about 13/32 in.;

the hollow conical tip of the inner hollow rod having an aperture;

the aperture of the hollow conical tip of the inner hollow rod being up to about ½ of the surface of the hollow conical tip;

the outer hollow rod being shorter in length than the inner hollow rod by about 3 in.;

the inner hollow rod being mounted in the outer hollow rod and rotatable about the axis of the inner and outer hollow rods;

said inner and outer hollow rods being rotatable to an open position and a closed position;

the open position being defined as the point where the apertures of the hollow conical tips of the inner and outer hollow rods are aligned so as to expose the cavity in the hollow conical tip of the inner hollow rod; and the closed position is the point where the inner and outer apertures of the inner and outer hollow conical tips are aligned so as not to expose the cavity in the hollow conical tip of the inner hollow rod.

A thief probe as described above, wherein the inner and outer hollow rod and their respective hollow conical tips are constructed from an non-reactive material.

A thief probe as described above, wherein the non-reactive material is selected from the group consisting of: aluminum, copper, steel and bronze.

A thief probe as described above, wherein the non-reactive material is aluminum.

A method for improved ending-sampling of a solid mixture comprising the steps of:

(a) inserting a thief probe, as described above, in the closed position into the solid mixture to a certain depth;

(b) rotating the inner hollow rod to the open position which allows a sample of the solid mixture to fill the cavity;

(c) inserting the thief probe in the open position to a certain depth so as to obtain the desired sample size;

(d) rotating the inner hollow rod to the closed position which allows a sample of the solid mixture to be trapped in the cavity; and (e) removing the thief probe from the solid mixture.

Several experiments were recently performed to assess the performance of two recently developed probes: a newly-released commercially available side sampling probe (Globe-Pharma, Piscataway, N.J.), and an end-sampling thief described in this application. The disturbances introduced by these probes were determined using two procedures:

1) A qualitative assessment of the extent of perturbation of the granular structure was performed by inserting the thief probes into a system which consisted of several alternate one-inch layers of white ($1500\mu$) and red ($600\mu$) glass beads. The granular beds were then solidified by infiltration with gelatin without removing the probes. The solidified beds were cut along the path of the probe and photographed.

2) Quantitative assessment of the errors introduced by each thief probe was carried out by sampling structures which consisted of two layers of differently-sized beads. The layered structure consisted of a 3 in. top layer over a 4 in. bottom layer. The beads were contained in cylindrical 6 in. diameter cans. The number of samples taken during each experiment was determined by the diameter of the probe being tested. A sampling grid was made for each probe, with each sampling location being at least two probe diameters away from any other sampling location. Two systems were considered: $60\mu$ beads on top of $200\mu$ beads, and $200\mu$ beads on top of $60\mu$ beads. Samples were taken at known positions above and below the interface between layers, and the composition of such samples was compared with the theoretical composition of the material at the sampling depth. In each case, samples were taken at locations far enough apart that the disturbances caused by previous insertions of the probe would not affect subsequent sampling.

Figure 7A:
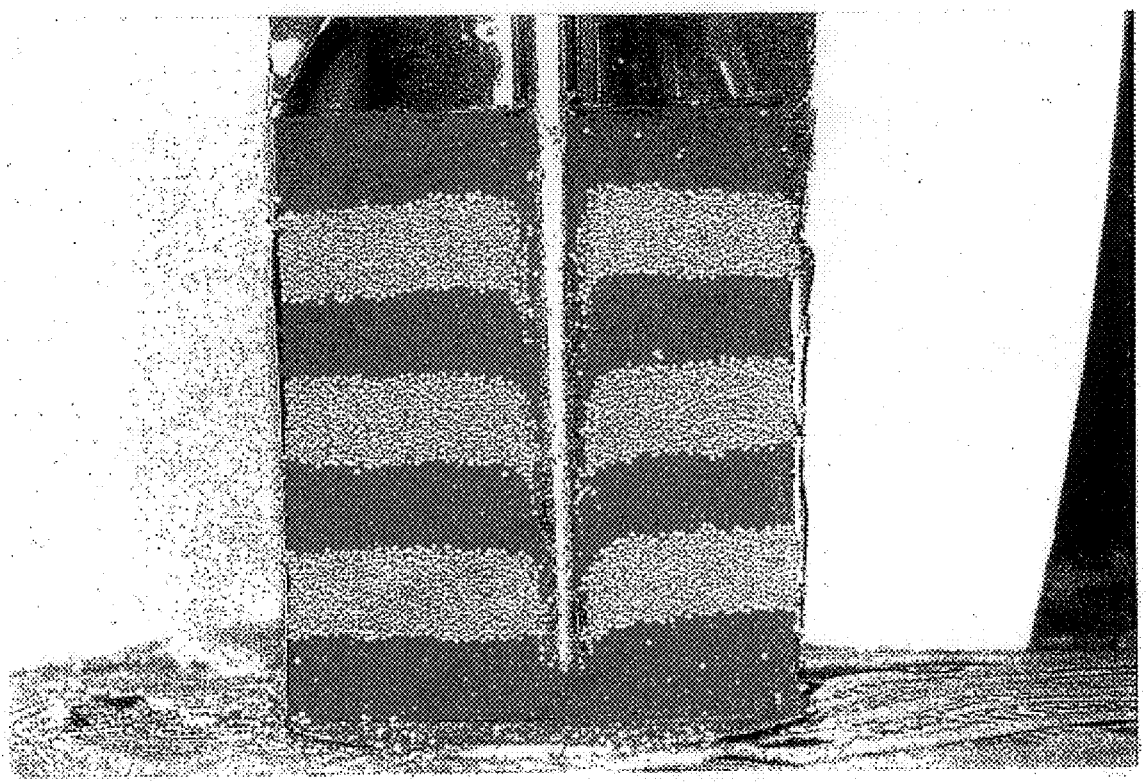
FIG. 7. Performance of the Globe Pharma thief probe. (a) Disturbances caused by insertion of the probe into particle bed (b) comparison of theoretical (---) and experimental (•,□) results for 60 $\mu$m particles over 200 $\mu$m particle and (c) 200 $\mu$m particles over 60 $\mu$m particles.

The Globe Pharma thief probe has a side-sampling design as described above. The thief probe has two cavities, and removable dies fit into the cavities in order to control sample volume. In all of the tests reported here, the lower cavity contained a 0.2 ml die while the upper one was filled with a solid die. Experiments showed that insertion of the Globe Pharma thief creates significant disturbances in the mixture (FIG. 7a). Particles from upper layers are dragged deeply into lower layers as the thief penetrates the granular bed. Once the thief is opened, the sample flowing into the thief will be contaminated with particles from positions along the path of insertion and will not necessarily reflect the true composition of the system at the sampling location before the thief was inserted.

Figure 7B:
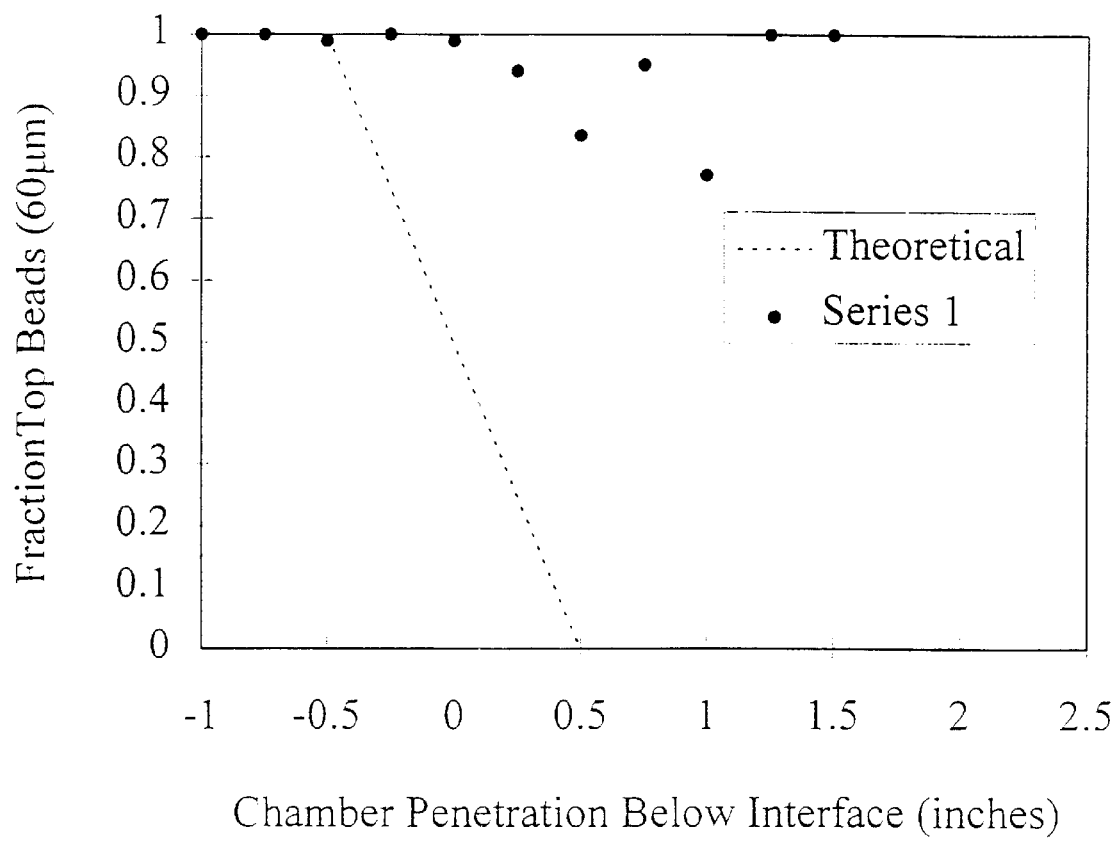
Figure 7C:
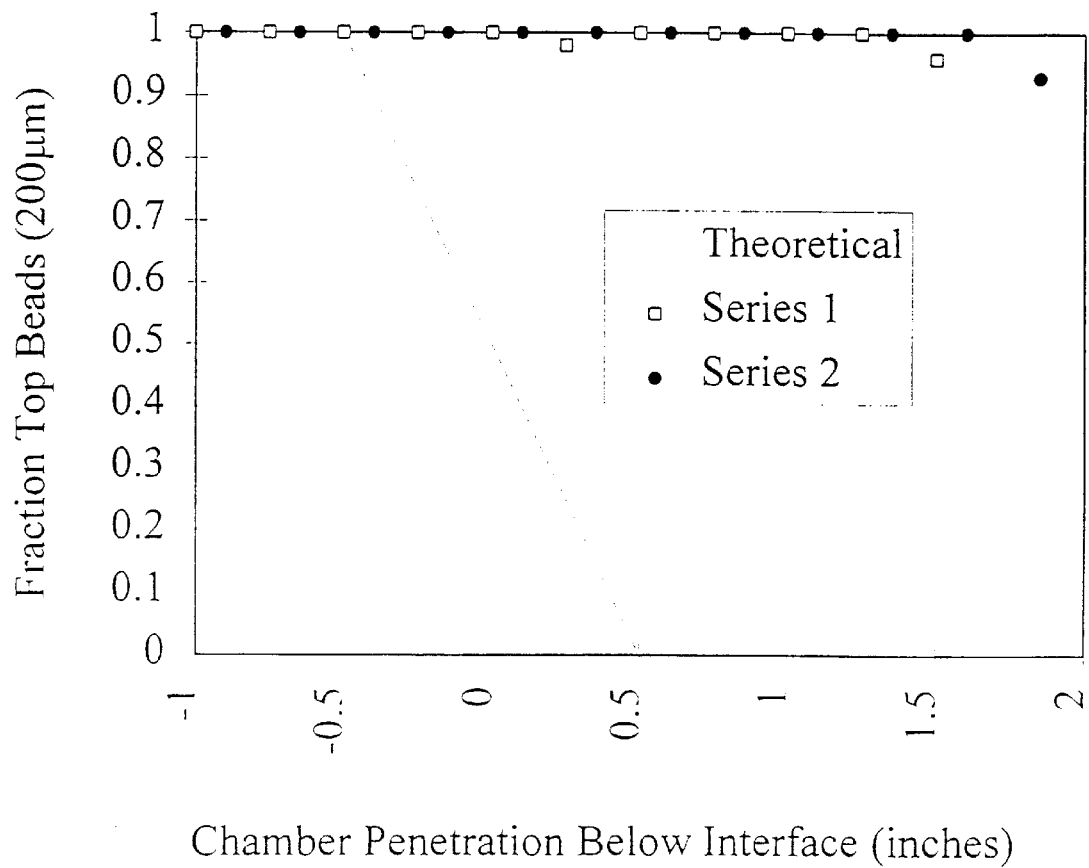

Other types of errors are also possible. Data comparing actual sample composition to theoretical composition expected from sampling location are shown in FIG. 7b and 7c for the Globe Pharma probe. The graphs show the percentage of the particles in the top layer that are contained in each sample. FIG. 7b shows results obtained for 60μ beads on top of 200μ beads, and FIG. 7c corresponds to 200μ beads on top of 60μ beads. If the probe accurately samples the desired location, the percentage of particles from the top layer should be zero once the opening crosses the interface between the top and bottom layers. However, as shown in FIGS. 7b and 7c, large sampling errors are incurred, and the samples are composed entirely of particles from the top layer regardless of sampling location. In order to identify the source of these errors, additional experiments were performed, in which the probe was introduced into the granular system and then removed without ever opening the cavity. Upon removal of the thief, it was observed that the cavity was filled with particles from the top layer. These experiments show that free-flowing materials can enter the cavity even before the Globe Pharma thief is opened. These errors could be magnified in industrial applications. In our experiments the thief was only inserted 3 to 5 inches below the upper surface of the granular bed, while in industrial sampling depths may be as much as several feet. If particles can flow into the thief while the cavity is closed, the resulting sample will be a composite of the system along the path of penetration of the thief, rather than the true composition of the undisturbed system.

Figure 8A:
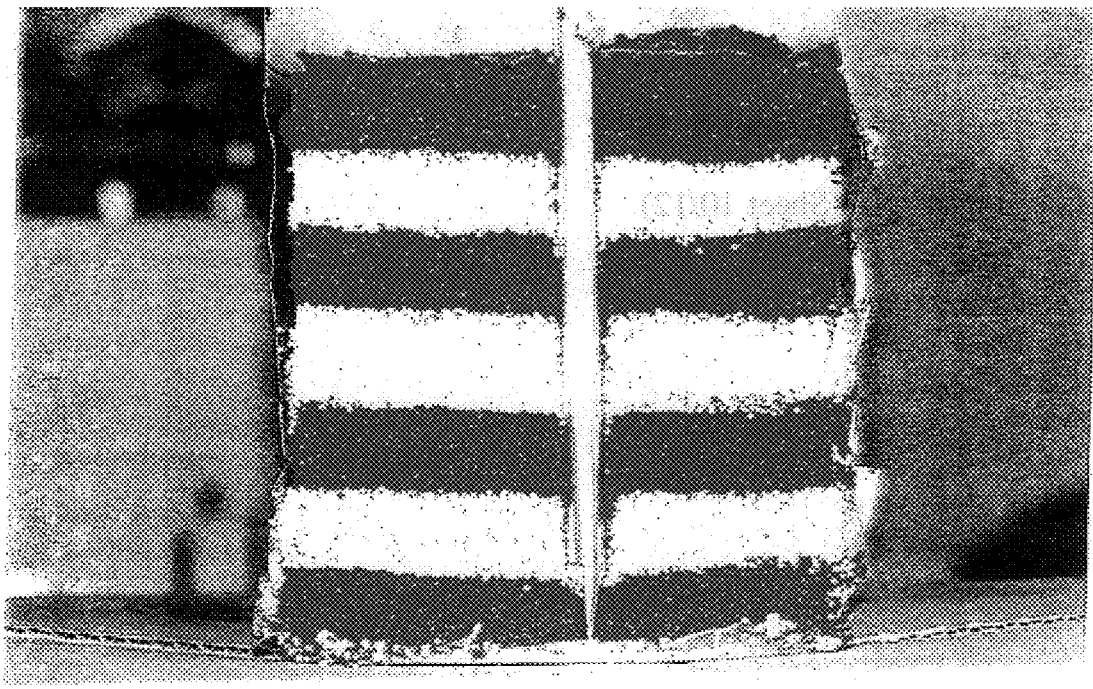
FIG. 8. Performance of the thief probe of the invention. (a) Minimum disturbances caused by insertion of the probe into particle bed (b) comparison of theoretical (---) and experimental (•,□,△) results for 60 $\mu$m particles over 200 $\mu$m particle and (c) 200 $\mu$m particles over 60 $\mu$m particles.

The second thief tested is an end-sampling thief. The thief probe consists of two concentric hollow pipes, both ending in a pointed cone (an inner and an outer rod each having a hollow conical tip) (FIG. 8a). Half of each cone has been removed (each hollow conical tip having an aperture) so that the sampling cavity of the thief can be set to an open position (when the aperture of the inner and outer hollow rods align so as to expose the cavity) and closed position (when the aperture of the inner and outer hollow rods align so as not to expose the cavity, the apertures are at 180 degrees to each other) by rotating the inner hollow pipe (inner hollow rod). The outer hollow rod having an inner diameter of about $7/16$ in. and an outer diameter of about $8/16$ in. and the inner hollow rod having an inner diameter of about $11/32$ in. and an outer diameter of about $13/32$ in. The length of the rods can be varied according to the depth of the vessel being sampled, however the outer hollow rod is shorter in length then the inner hollow rod by about 3 in. The thief can be constructed from any material which will not react with the samples being taken. Examples of such materials are aluminium, copper, steel and bronze. The material used to construct the thief used in the experiments described is aluminium. Additionally, it should be noted that the clearance between the inner and outer hollow rods should be minimized. However, if the clearance allows for particles to flow into the thief when in the closed position, a gasket can be employed to fill in this clearance and prevent this from occurring.

Figure 4:
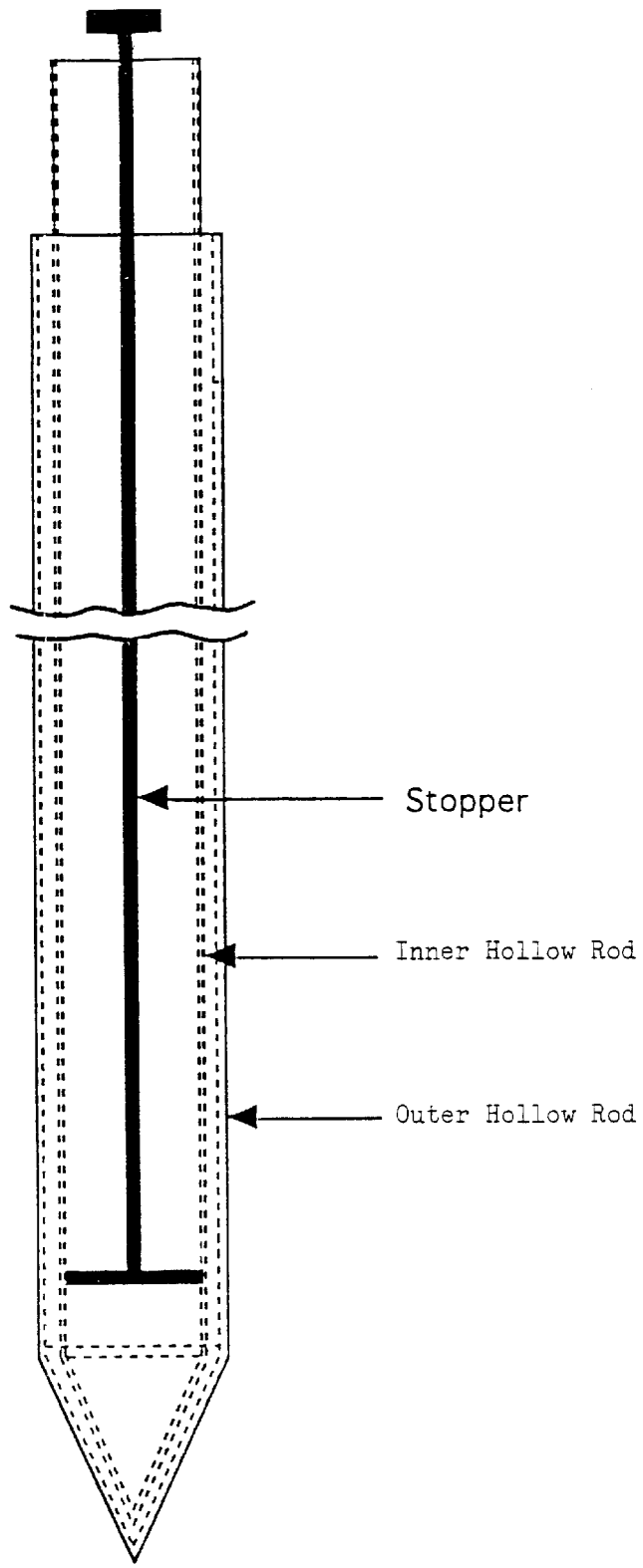
FIG. 4. Schematic of the inner hollow rod with a inner conical tip mounted in the outer hollow rod with a outer conical tip of the thief probe of the invention with a stopper (front view).
Figure 5:
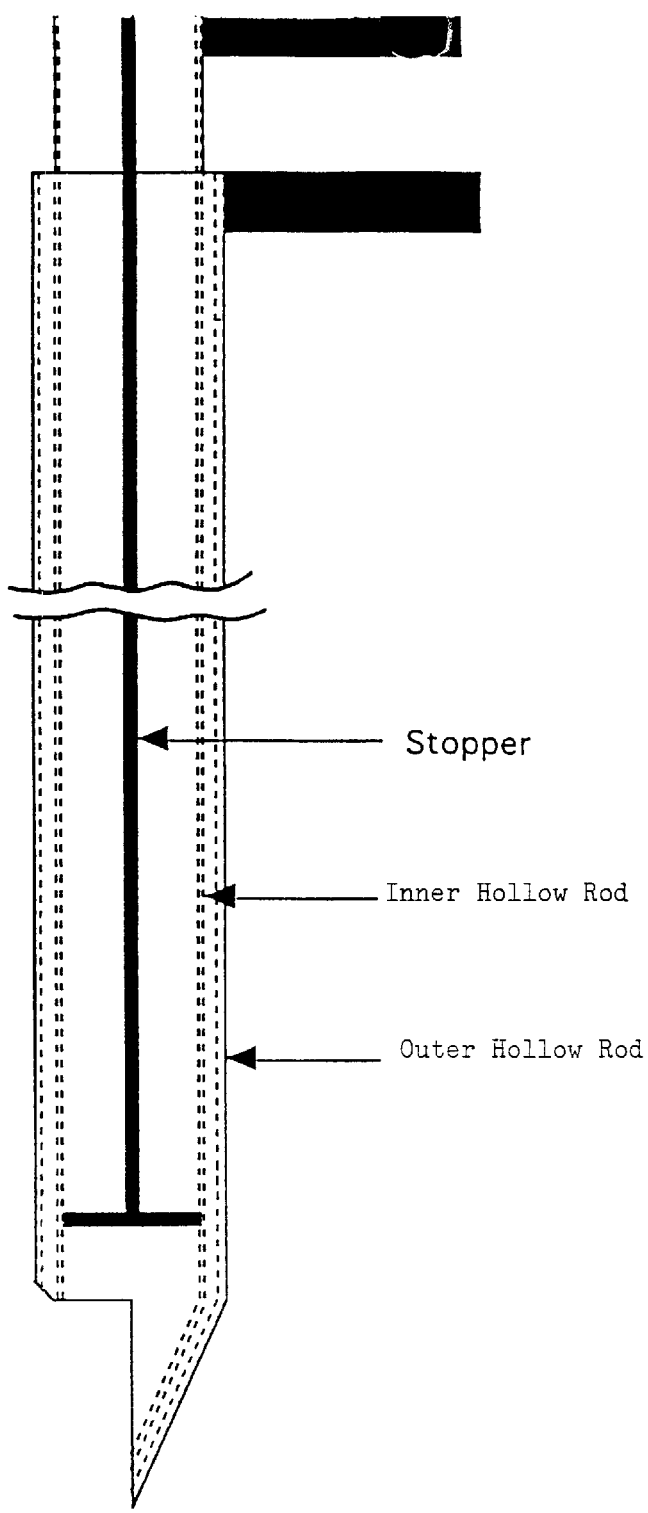
FIG. 5. Schematic of the inner hollow rod with a inner conical tip mounted in the outer hollow rod with a outer conical tip of the thief probe of the invention with a stopper in the open position (side view).
Figure 6:
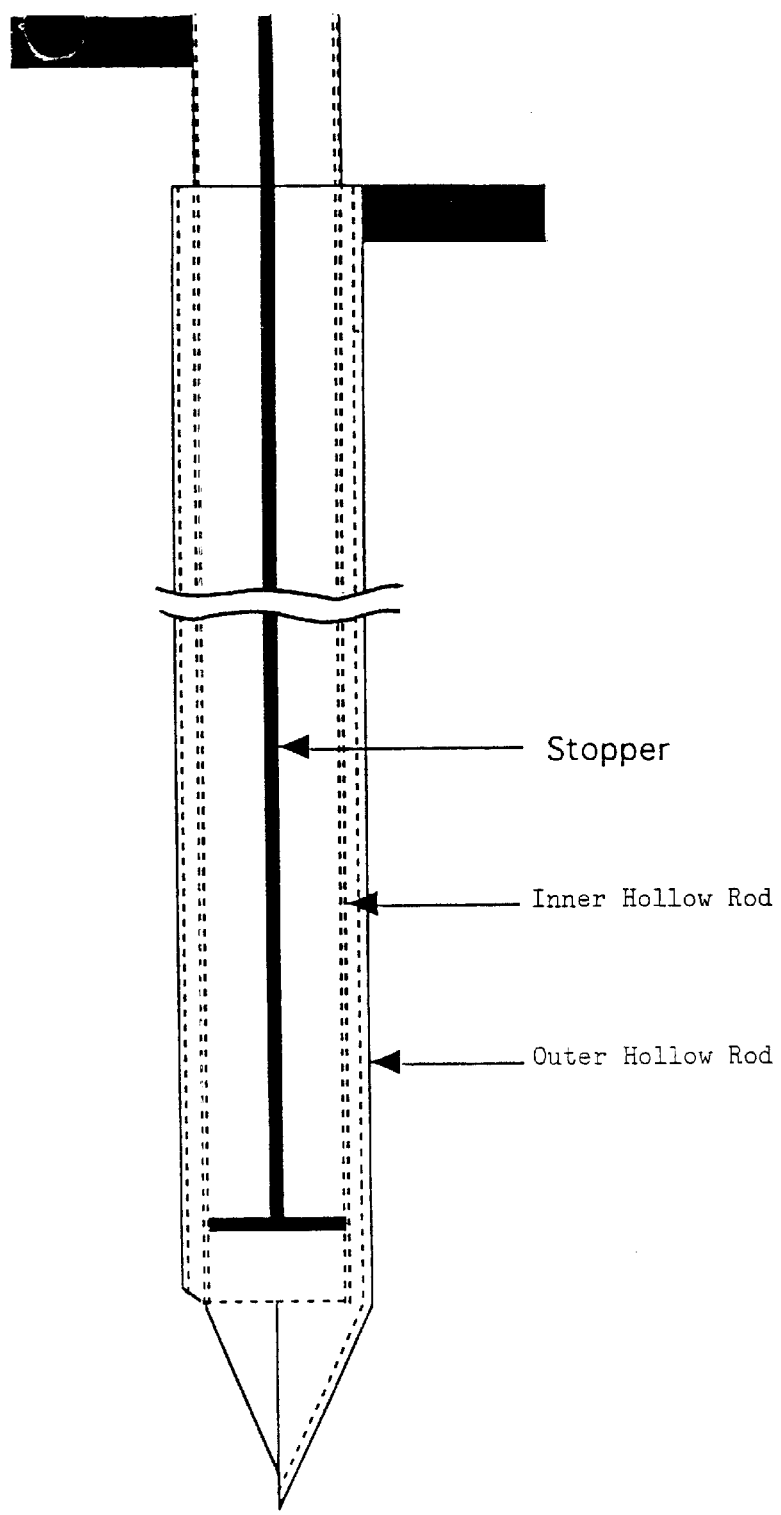
FIG. 6. Schematic of the inner hollow rod with a inner conical tip mounted in the outer hollow rod with a outer conical tip of the thief probe of the invention with a stopper in the closed position (side view).
Figure 8B:
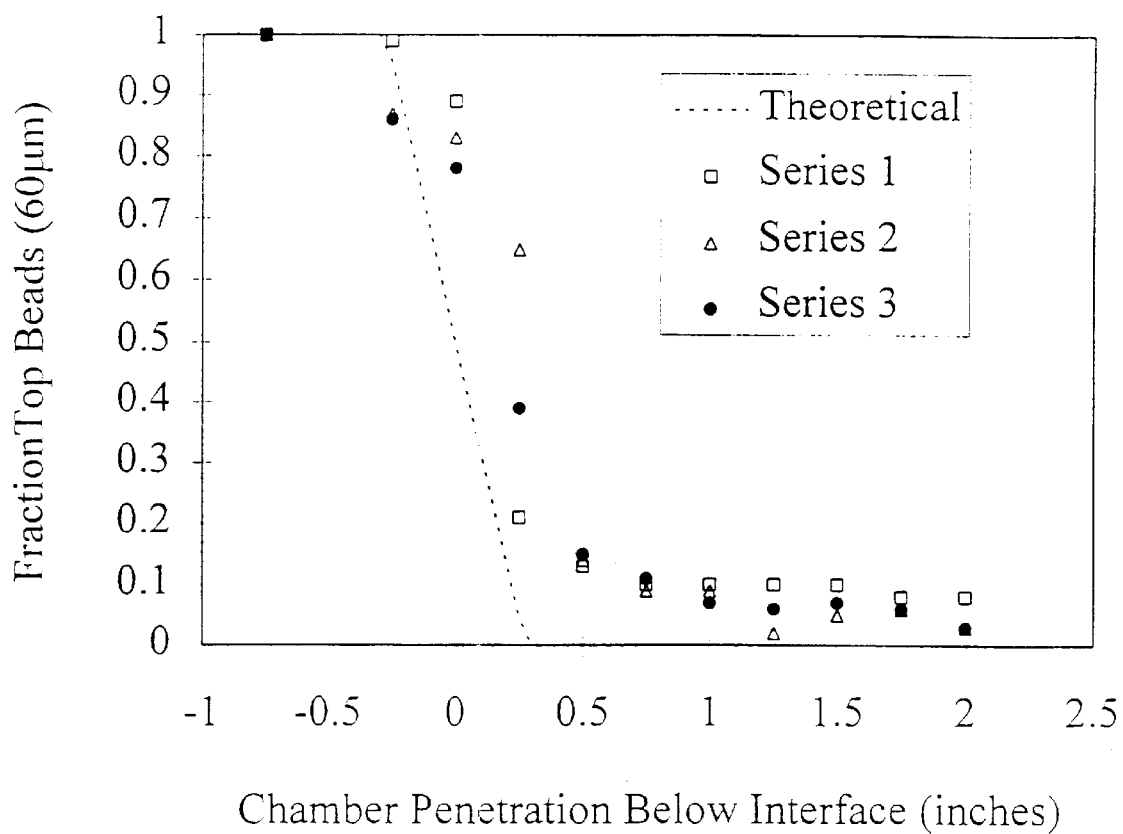
Figure 8C:
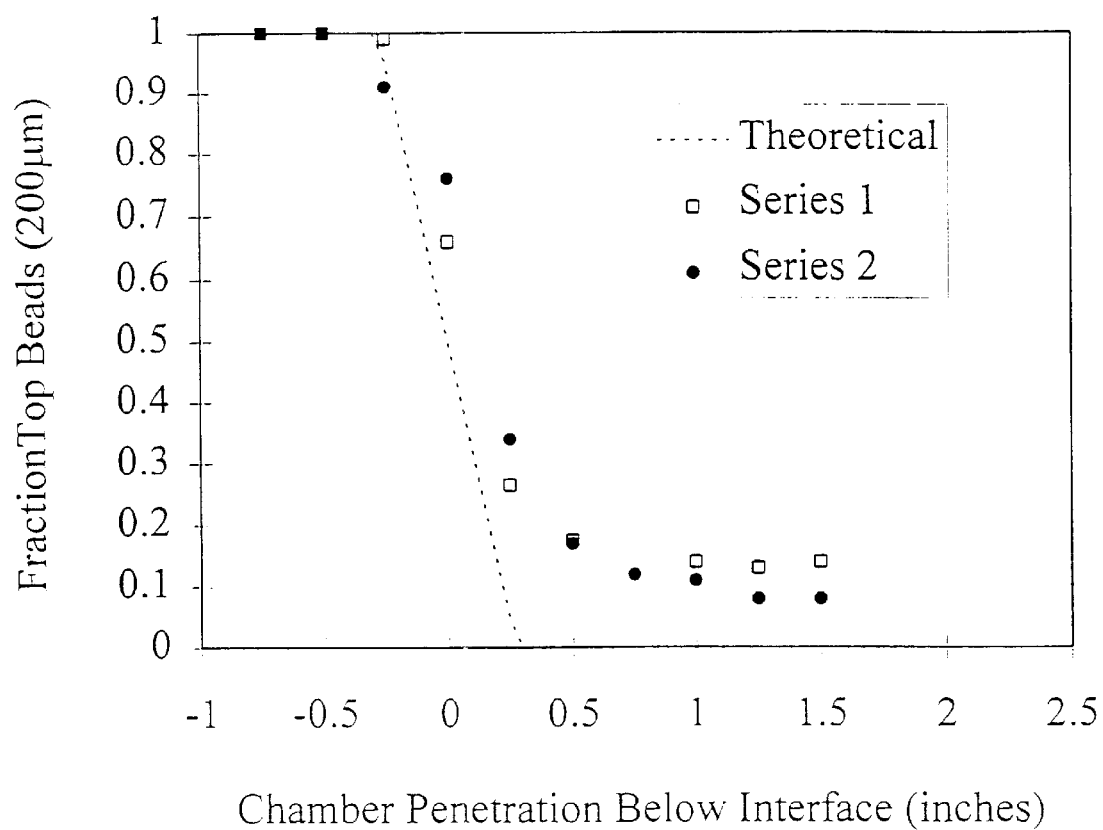

The thief is used as follows: the thief is inserted in the closed position into a vessel containing a powder mixture to be sampled to the desired depth, the inner hollow rod is rotated to the open position exposing the cavity of the inner hollow conical tip, the thief is inserted further into the powder bed, the inner hollow rod is rotated to the closed position closing the cavity of the inner hollow conical tip, and then the thief containing a sample of the powder mixture is removed from the mixture. Samples of consistent size were obtained by controlling the depth of insertion after the cavity of the thief probe is opened, as well as the diameter of the thief probe. Additionally, a stopper may be used to set the sample size, as shown in FIG. 4–6. As shown in FIG. 8a, the pointed cone design of this thief introduces much smaller disturbances of the granular structure than the previous device. Disturbances are minimal near the tip of the probe, where the sampling takes place. Quantitative comparison of theoretical and experimental sampling data is shown in FIG. 8b for 60μ particles on top of 200μ particles, and in FIG. 8c for 200μ particles on top of 60μ particles. The data indicates that the thief probe of the invention performs much better than the Globe Pharma thief probe.

What is claimed is:

1. A thief probe comprising an outer hollow rod with a hollow conical tip attached at one end of the outer hollow rod and an inner hollow rod with a inner hollow conical tip attached at one end of the inner hollow rod;

said outer hollow rod having an inner diameter of about ¼ in. to about $63/32$ in. and an outer diameter of about $9/32$ in. to about 2 in.;

the hollow conical tip of the outer hollow rod having an aperture;

the aperture of the hollow conical tip of the outer hollow rod being ½ of the surface of the hollow conical tip;

said inner hollow rod having an inner diameter of about $7/32$ in. and an outer diameter of about $62/32$ in.;

the hollow conical tip of the inner hollow rod having an aperture;

the aperture of the hollow conical tip of the inner hollow rod being ½ of the surface of the hollow conical tip;

the outer hollow rod being shorter in length than the inner hollow rod by about 3 in.;

the inner hollow rod being mounted in the outer hollow rod and rotatable about the axis of the inner and outer hollow rods;

said inner and outer hollow rods being rotatable to an open position and a closed position;

the open position being defined as the point where the apertures of the hollow conical tips of the inner and outer hollow rods are aligned so as to expose a cavity in the hollow conical tip of the inner hollow rod; and the closed position is the point where the inner and outer apertures of the inner and outer hollow conical tips are aligned so as not to expose the cavity in the hollow conical tip of the inner hollow rod.

2. A thief probe comprising an outer hollow rod with a hollow conical tip attached at one end of the outer hollow rod and an inner hollow rod with a inner hollow conical tip attached at one end of the inner hollow rod;

said outer hollow rod having an inner diameter of about ¼ in. to about $63/32$ in. and an outer diameter of about $9/32$ in. to about 2 in.;

the hollow conical tip of the outer hollow rod having an aperture;

the aperture of the hollow conical tip of the outer hollow rod being ½ of the surface of the hollow conical tip;

said inner hollow rod having an inner diameter of about $7/32$ in. to about $61/32$ and an outer diameter of about $8/32$ in. to about $62/32$;

the hollow conical tip of the inner hollow rod having an aperture;

the aperture of the hollow conical tip of the inner hollow rod being ½ of the surface of the hollow conical tip;

the outer hollow rod being shorter in length than the inner hollow rod by about 3 in.;

an inner solid rod having a diameter of $6/32$ in. to about $60/32$ in.;

said inner solid rod being mounted in the inner hollow rod and being adjustable in height, so as to define the size of a cavity of the inner hollow rod;

the inner hollow rod with the mounted inner solid hollow rod being mounted in the outer hollow rod and rotatable about the axis of the inner and outer hollow rods;

said inner and outer hollow rods being rotatable to an open position and a closed position;

the open position being defined as the point where the apertures of the hollow conical tips of the inner and outer hollow rods are aligned so as to expose the cavity in the hollow conical tip of the inner hollow rod; and the closed position is the point where the inner and outer apertures of the inner and outer hollow conical tips are aligned so as not to expose the cavity in the hollow conical tip of the inner hollow rod.

3. The thief probe as recited in claim 1, comprising an outer hollow rod with a hollow conical tip attached at one end of the outer hollow rod and an inner hollow rod with a inner hollow conical tip attached at one end of the inner hollow rod;

said outer hollow rod having an inner diameter of about 7/16 in. and an outer diameter of about 8/16 in.;

the hollow conical tip of the outer hollow rod having an aperture;

the aperture of the hollow conical tip of the outer hollow rod being ½ of the surface of the hollow conical tip;

said inner hollow rod having an inner diameter of about 11/32 in. and an outer diameter of about 13/32 in.;

the hollow conical tip of the inner hollow rod having an aperture;

the aperture of the hollow conical tip of the inner hollow rod being ½ of the surface of the hollow conical tip;

the outer hollow rod being shorter in length than the inner hollow rod by about 3 in.;

the inner hollow rod being mounted in the outer hollow rod and rotatable about the axis of the inner and outer hollow rods;

said inner and outer hollow rods being rotatable to an open position and a closed position;

the open position being defined as the point where the apertures of the hollow conical tips of the inner and outer hollow rods are aligned so as to expose the cavity in the hollow conical tip of the inner hollow rod; and the closed position is the point where the inner and outer apertures of the inner and outer hollow conical tips are aligned so as not to expose the cavity in the hollow conical tip of the inner hollow rod.

4. The thief probe as described in claim 1, wherein the inner and outer hollow rod and their respective hollow conical tips are constructed from an non-reactive material.

5. The thief probe as described in claim 4, wherein the non-reactive material is selected from the group consisting of: aluminum, copper, steel and bronze.

6. The thief probe as described in claim 5, wherein the non-reactive material is aluminum.

* * * * *